(12) United States Patent
Brown et al.

(10) Patent No.: US 6,352,719 B1
(45) Date of Patent: Mar. 5, 2002

(54) CAPSULE BASED DRUG DELIVERY SYSTEM

(75) Inventors: Malcolm David Brown, Mundford; Barry John Muncaster, Milton; Edward Zbygniew Nowak, Impington, all of (GB)

(73) Assignee: Bioprogress Technology International, Inc., Atlanta, GA (US)

( * ) Notice: Subject to any disclaimer, the term of this patent is extended or adjusted under 35 U.S.C. 154(b) by 0 days.

(21) Appl. No.: 09/831,587

(22) PCT Filed: Nov. 4, 1999

(86) PCT No.: PCT/GB99/03649

§ 371 Date: Jun. 15, 2001

§ 102(e) Date: Jun. 15, 2001

(87) PCT Pub. No.: WO00/27367

PCT Pub. Date: May 18, 2000

(51) Int. Cl.[7] .......................... A61K 9/48; A61K 47/00; A61K 9/54; A61K 9/14

(52) U.S. Cl. .................. 424/463; 424/439; 424/451; 424/458; 424/485; 424/488

(58) Field of Search .................. 424/463, 439, 424/451, 458, 485, 488

(56) References Cited

U.S. PATENT DOCUMENTS 5,254,294 A * 10/1993 Wunderlich et al. ........... 264/4

FOREIGN PATENT DOCUMENTS

| FR | 2 757 173 | * 12/1996 |
| JP | 59071673 | * 4/1994 |

* cited by examiner

*Primary Examiner*—Thurman K. Page
*Assistant Examiner*—Blessing M. Fubara
(74) *Attorney, Agent, or Firm*—Morgan & Finnegan, LLP

(57) ABSTRACT

A soft capsule comprising a wall derived from a multilayer film that comprises three layers. The layers are an innermost sealing plasticized hydroxypropyl methyl cellulose, an adhesion promoting layer of propylene glycol alginate and a barrier layer of sodium alginate.

19 Claims, 1 Drawing Sheet

CAPSULE BASED DRUG DELIVERY SYSTEM

FIELD OF THE INVENTION

This invention relates to soft capsules for drug delivery systems.

BACKGROUND TO THE INVENTION

The provision of soft capsules containing pharmaceutical preparations is well established. Typically, drugs and dietary supplements are encapsulated is soft or hard gelatin shells designed to release their contents under specific conditions encountered in the body. The gelatin shells used for these capsules are derived from animal renderings.

With concerns of animal related diseases such as Bovine Spongiform Encephalopathy (BSE), and the existence of large groups of the population unable or unwilling to take animal based products for religious or ethical reasons, there is a profound need for a substitute material for soft capsule shells. However the machinery used in the production of gelatin capsules does not lend itself to the use of alternative materials, particularly those suitable for ingestion. In addition those materials which perform in a similar fashion mechanically to gelatin do not have suitable barrier properties to prevent spoilage of certain sensitive ingredients. As a result it is necessary to change not only the capsule material, but also the machinery used for their production. It is this change in material and the necessary processing means which this invention addresses, by producing soft capsules with good barrier properties and optional controlled release.

SUMMARY OF THE INVENTION

According to the invention there is provided a soft capsule comprising a wall derived from a multilayer film comprising of three layers, namely a sealing layer of plasticised hydroxy propyl methyl cellulose, an adhesion-promoting layer of propylene glycol alginate and a barrier layer of sodium alginate.

The encapsulating films have robust mechanical properties and good oxygen barrier when used as a capsule wall. The films created are preferably but not essentially coated to achieve precise drug delivery and protection of their contents and use a carrier membrane which also acts as the sealing layer. The sealing layer is typically a modified cellulose 18 to 200 microns thick and soluble in cold water. The coatings control the time and site of release of the finished capsules as well as offering specific barrier properties to prevent the spoilage of the capsule contents. The conversion process involves film transport, coating, vacuum forming, filling, sealing and cutting.

The materials used to coat the surface of the cellulose sealing layer include sodium alginates, propylene glycol alginate, pectins, gellan gums, carrageenans, xanthan gum, locust bean gum, starches, soy protein, gluten and derivatives such as Arainoxylan ferulyate (AXF), zein, and gum arabic. These materials can be applied to the surface either before the film is made into capsules, or as a finishing treatment to pre made capsules. The selection of the preferred coating material is determined by the properties, contents and release characteristics required of the finished capsule. In order to provide flexibility these coating materials can be plasticised with agents such as glycerine or mono propylene glycol. A plasticiser to polymer ratio of 1:1 has been found to impart good flexibility for capsule manufacture. Where the agents are applied as a post treatment this plasticiser content can be significantly reduced.

One or more of the three layers are preferably deformable by heat, providing between them the means for sealing and good oxygen barrier. These three layers function well over a wide range of individual thickness. The ratio is selected according the type of processing, capsule content, and capsule end application. In a typical oil bearing ingestible soft capsule the carrier or sealing membrane is hydroxy methyl cellulose plasticised with glycerine and propylene glycol or mono, di or tri acetin at a thickness of 10 to 150 microns, and the upper barrier layer is sodium alginate at a thickness of 5 to 50 microns plasticised with glycerine or sorbitol. In order to achieve a good level of adhesion between these layers a tie layer promoting adhesion consisting of propylene glycol alginate in the region of 0.5 to 20 microns is present.

It is preferred that the sealing layer is deformable by heat and seals using the established processes of heat, radio frequency or a combination of both. Alternatively, high frequency, ultrasonic or induction welding can be employed as the sealing method. Good results have been achieved using hydroxy methyl propyl cellulose plasticised with glycerine and propylene glycol at 100 microns as a sealing layer with radio frequency as the sealing method.

To secure a barrier layer to the sealing layer sufficiently well that it will survive the rigors of the capsule forming process without delamination it has been found necessary and beneficial to use an adhesion promoter or tie layer. Propylene glycol alginate improves the adhesion of sodium alginate to hydroxy propyl methyl cellulose, as does a 50:50 blend of propylene glycol alginate and hydroxy propyl methyl cellulose. The materials used in the tie layer may also be plasticised with such materials as glycerine and or mono propylene glycol at around 20%. In this invention propylene glycol alginate has been found to perform this function well at a thickness of 4 microns.

The top layer provides the means to obtain specific barrier properties as well as time and site release such as area within the body in the case of ingestion. Time release can be controlled by thickness, but site release often needs formulation modifications. When sodium alginate or pectin is used as the barrier layer it can be made partially soluble by introducing the surface to calcium ions thus forming a thin water insoluble layer which can be made to dissolve slowly in the presence of sequestering agents or when there is a change in pH.

The multi layered capsule shell film is prepared by coating the innermost sealing layer with an adhesion layer and a barrier or dissolution controlling layer. These coatings can be applied by roller, Meyer bar, dipping, spraying, electrostatically, extrusion, sponge, gravure, or flexo.

The preparation of the multi layered film can occur within the capsule manufacturing unit or off line whereby the finished multi layered film is supplied to a dedicated processing unit. It may also be formed by the application of the tie layer and barrier layer to capsules formed exclusively from the sealing layer. Where this application occurs off line as a post formed treatment by such methods as spray drying, dusting or coating, gum arabic, AXF, sugars, polyols and waxes have been found to work well.

The ability to seal any of the films described in this patent by heat inducing methods, including radio frequency, and the ability to produce strong finished seals can be enhanced by the application of certain materials, namely water soluble glycols, alcohols, lactones, acetins and pyrrolidones to the surface of the sealing layer. These materials also help to form a seal where the surface of the sealing layer is contaminated with oil. Propylene glycol, propanol, ethanol, butyrolactone, n-methyl pyrrolidone and gamma valerolactone have been found to work well in this case.

A preferred method of encapsulation is characterised by supplying a multi layered film to a dedicated encapsulation unit capable of deforming the film into two capsule halves, filling, sealing and cutting.

In the encapsulation unit the film is pre formed preferably by the use of vacuum into capsule halves and the substance to be encapsulated is supplied between the films where it enters the two pre formed capsule halves during closing.

The pre forming process may be enhanced by heating the forming head, or film to an elevated temperature of around 80–120° C. In order to minimise the exposure of the capsule fill to high temperatures it is preferred that the film is heated just prior to capsule formation rather than the capsule forming head.

The encapsulation unit typically consists of a pair of flat forming heads or drums, where at least one of pair is formed with a plurality of indentations the size of the desired finished capsule on their face. Means for applying a vacuum to these forming heads is conveniently included, to help pull the film into the indentations and so assist in capsule formation. These heads are supplied by rolls of film which may be coated with several applications before reaching them. The pre formed capsules are filled while inside the forming heads before being sealed by the application of recognised and established methods, namely heat, radio frequency or a combination of these two. After sealing the capsules are cut out and ejected.

Whilst it is a preferred feature that the forming, filling, sealing and cutting occur at the same location it may also occur as a stepped process whereby the capsules are pre formed and filled at a different location to where they are sealed and where they are cut.

The invention will further be described, by way of example, with reference to the accompanying drawings, in which.

DETAILED DESCRIPTION OF THE DRAWINGS

Figure 1:
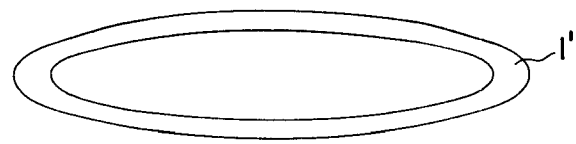
FIG. 1 is a schematic representation of a capsule.

FIG. 1 illustrates a capsule with a substance encapsulated by a shell wall 1'.

Figure 2:
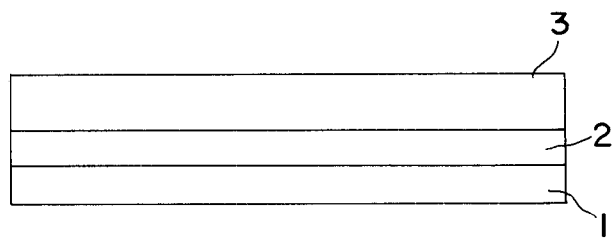
FIG. 2 is a schematic representation of the preferred multi-layer film of a capsule according to the invention.

The capsule shell wall or membrane illustrated in FIG. 2 comprises three layers. The sealing layer 1 is hydroxy propyl methyl cellulose plasticised with glycerine at 10% and propylene glycol at 18%, present at 100 microns. The top layer is a barrier layer 3, and is sodium alginate plasticised with glycerine or sorbitol at 50%, present at a thickness of 10 microns. In between these layers 1 and 3 is an intermediate sealing layer 2, helping adhesion, and made of propylene glycol alginate, present at a thickness of 4 microns. This intermediate layer 2 may also contain a plasticiser up to 50%.

The three layer wall or membrane is prepared by a series of two coatings from solution or by extrusion on to the surface of pre formed plasticised hydroxy propyl methyl cellulose film. The propylene glycol alginate is applied first followed by the plasticised sodium alginate. The coatings are applied separately by means of coating heads onto the surface of the hydroxy propyl methyl cellulose film on conventional coating apparatus. The three layer film can then be supplied to the encapsulation unit pre formed in rolls.

Figure 3:
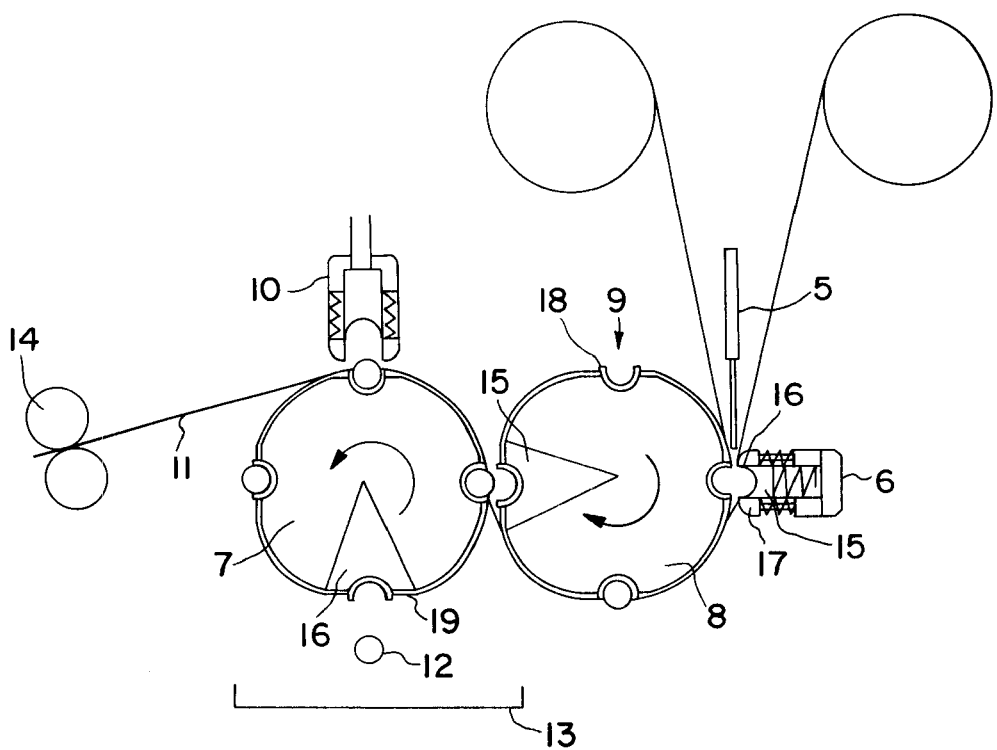
FIG. 3 is a schematic illustration of a manufacturing unit for making the capsule.

FIG. 3 shows a capsule processing unit where the cutting process occurs remotely from the forming heads. From the two reels at the top of FIG. 3, two lengths of multi-layer film are fed to the forming heads. The female forming head and cutting area are located in a cylinder, with flat faces exampled by 19, either side of the capsule forming areas exampled by 9. The female forming areas have raised side walls, 18, which help in the channelling of excess liquid fill away from the filling area. As the cutting does not take place at the point of capsule formation the female forming unit is not sprung. Film passes over the forming head 6 and the forming drum 8. Vacuum is applied to draw the film into the forming heads. Forming head 6 has a forming cup 15 with a small groove cut in it, and has a grooved stripper plate assembly. The filling injector 5 comes down and is then engulfed by the stripper plate groove 16 in the stripper plate 17. The filling injector 5 then withdraws as it fills the pre formed capsule. When the injector 5 has fully withdrawn, a further forward motion by forming head 6 causes a seal to be made. This seal is completed by the action of heat, radio frequency or a combination of these two. When the capsule is made and filled the forming head 6 moves away from the forming drum 8 and the drum rotates to present another forming cup. The filled capsule which has not been cut remains held in place in the forming drum 8 by means of vacuum. This capsule remains in the forming drum 8 until it is passed to cutting drum 7. This occurs by means of a loss in vacuum on the forming drum 8, shown by the indicated area 15, and the presence of vacuum in the cutting drum 7. The formed capsule passes over the cutting head 10, where by means of a punch action it is cut free from the surrounding film. The finished capsule 12 remains in the cutting drum 7 until it drops into the tray 13 when vacuum on the cutting drum 7 is released in the indicated area 16. The waste film 11 with holes is transported via the rollers 14 to waste.

EXAMPLE

By using the multilayer film shown in FIG. 2 in the apparatus of FIG. 3, good quality soft capsules were produced suitable for ingestion.

What is claimed is:

1. A soft capsule comprising a wall derived from a multilayer film comprising three layers, namely a sealing layer of plasticised hydroxy propyl methyl cellulose, an adhesion-promoting layer of propylene glycol alginate and a barrier layer of sodium alginate.

2. A soft capsule according to claim 1, wherein the layer made from hydroxy propyl methyl cellulose is an innermost sealing layer.

3. A soft capsule according to claim 1 or 2, wherein the sealing layer is sealed by means of radio frequency, ultrasonics or induction heat sealing.

4. A soft capsule according to claim 1 or 2, wherein the sealing layer is sealed by means of heat.

5. A soft capsule according to claim 1 or 2, wherein sealing of the film is enhanced by application to the sealing layer of an alcohol.

6. A soft capsule according to claim 1 or 2, wherein sealing of the film is enhanced by application to the sealing layer of a glycol.

7. A soft capsule according to claim 1 or 2, wherein sealing of the film is enhanced by application to the sealing layer of a lactone.

8. A soft capsule according to claim 1 or 2, wherein sealing of the film is enhanced by application to the sealing layer of a pyrrolidone.

9. A soft capsule according to claim 1 or 2, wherein sealing of the film is enhanced by application to the sealing layer of an acetin.

10. A soft capsule according to claim 6, wherein the material used to enhance sealing is mono propylene glycol.

11. A soft capsule according to claim 1 or claim 2, wherein the capsule is coated after formation with gum arabic.

12. A soft capsule according to claim 3, wherein the capsule is coated after formation with gum arabic.

13. A soft capsule according to claim 4, wherein the capsule is coated after formation with gum arabic.

14. A soft capsule according to claim 5, wherein the capsule is coated after formation with gum arabic.

15. A soft capsule according to claim 6, wherein the capsule is coated after formation with gum arabic.

16. A soft capsule according to claim 7, wherein the capsule is coated after formation with gum arabic.

17. A soft capsule according to claim 8, wherein the capsule is coated after formation with gum arabic.

18. A soft capsule according to claim 9, wherein the capsule is coated after formation with gum arabic.

19. A soft capsule according to claim 10, wherein the capsule is coated after formation with gum arabic.

* * * * *